(12) United States Patent
Howlett

(10) Patent No.: US 7,513,894 B2
(45) Date of Patent: Apr. 7, 2009

(54) HUMAN BODY FLUID COLLECTION BAG

(76) Inventor: Jim Howlett, P.O. Box 6258, Abilene, TX (US) 79608

( * ) Notice: Subject to any disclaimer, the term of this patent is extended or adjusted under 35 U.S.C. 154(b) by 432 days.

(21) Appl. No.: 11/404,547

(22) Filed: Apr. 14, 2006

(65) Prior Publication Data
US 2006/0189957 A1    Aug. 24, 2006

Related U.S. Application Data

(63) Continuation-in-part of application No. 10/887,763, filed on Jul. 8, 2004, now abandoned.

(51) Int. Cl.
*A61F 5/44* (2006.01)
(52) U.S. Cl. .............. 604/355; 604/317; 604/327; 604/328
(58) Field of Classification Search ............ 604/355
See application file for complete search history.

(56) References Cited

U.S. PATENT DOCUMENTS

| | | | | | |
|---|---|---|---|---|---|
| 2,380,740 | A | * | 7/1945 | Fenwick | 604/334 |
| 4,180,072 | A | * | 12/1979 | Sneider | 604/32 |
| 4,784,656 | A | * | 11/1988 | Christian | 604/355 |
| 5,520,669 | A | * | 5/1996 | Mulholland | 604/328 |
| 7,131,964 | B2 | * | 11/2006 | Harvie | 604/347 |
| 2002/0193762 | A1 | * | 12/2002 | Suydam | 604/327 |

* cited by examiner

*Primary Examiner*—Tatyana Zalukaeva
*Assistant Examiner*—Ginger T Chapman
(74) *Attorney, Agent, or Firm*—Charles D. Gunter, Jr.

(57) ABSTRACT

The collection bag of the invention is used to capture body fluids/waste material throughout the complete process as an enema is being administered, eliminating contamination of the patient, bed, linens, and floor as well as the caregiver and others that administer the enema. This bag can be administered to patients that are recovering from bariatric surgery, are in a long term care facility, hospital, home, or special unit caring for spinal cord injuries, or head injuries. It can be used with patients who are in a comatose condition whereby hip flexion, weight bearing, or transferring to a bedside commode is impossible. This collection bag captures waste for laboratory testing and other lab work and is marked with warning indicia. The bag fits any age patient, male or female.

4 Claims, 3 Drawing Sheets

HUMAN BODY FLUID COLLECTION BAG

CROSS REFERENCE TO RELATED APPLICATIONS

The present application is a continuation-in-part of my earlier filed application, Ser. No. 10/887,763, filed Jul. 8, 2004 now abandoned, entitled "Enema Body Fluid Collecting Bag."

BACKGROUND OF THE INVENTION

1. Field of the Invention

The present invention relates in general to disposable medical accessories and, in particular to disposable bags for the collection and monitoring of body fluids resulting from the administration of water or other therapeutic agents into the bowel through the rectum, such as might be encountered in giving a patient an enema.

2. Description of the Prior Art

One common problem with aged or infirm persons is the tendency to have fecal impactions, thereby necessitating an enema or some other similar procedure for relief. Prior art devices for providing an enema or otherwise irrigating the person's bowel leave much to be desired from the standpoint of sanitation and ease of use. In these situations, containment of the fecal matter in collecting and handling such matter presents a continuing problem. Conventional bed pans or other rigid containers, with or without additional draping, put the patient in an uncomfortable position, frequently requiring untenable maneuvers, and often resulting in unsanitary conditions as well as unpleasant odors. Concern for better containment of and sanitation has become heightened recently in handling of patients with Acquired Immune Deficiency Syndrome (AIDS), whose fecal matter may contain infected blood.

Another area of concern is in the treatment of bariatric surgical patients. Bariatric surgery is a widely recognized method of achieving long term weight control for the morbidly obese by surgically reducing the size of the gastric reservoir. A need for improved collection devices arises not only in these types of common situations, but also in intensive care units, other surgical settings, and settings including nursing homes and geriatric care facilities, and whenever non-ambulatory patients require assistance in this regard.

A need accordingly exists for a disposable body fluid collecting bag which is simple in design and economical to manufacture which overcomes many of the previously noted deficiencies of the prior art devices.

SUMMARY OF THE INVENTION

The principle object of the present invention is therefore to provide an improved body fluid collecting bag which overcomes many of the difficulties present in the present state of the art devices, as previously discussed.

It is yet another object of the present invention to provide such a collecting bag which is both sanitary and easily disposable, and which is relatively simple to use and sufficiently cheap to manufacture in order to meet the single use, throw-away concept of modern day medicine.

It is yet another object of the present invention to provide a collecting bag which can be easily replaced by relatively untrained individuals, without pain or other such difficulties to the patient, and which can be used without causing undue irritation or infection.

It is yet another object of the present invention to provide a collecting bag which helps to eliminate spills, odors and other such difficulties resulting from leakage associated with the involuntary and uncontrolled expelling of feces by such patients.

It is yet another object of the present invention to provide a collecting bag which eliminates the transmission of bacteria and bacterial infections, and which can be used in connection with the analysis of excretions from various body openings.

It is yet another object of the present invention to provide a collecting bag which can be advantageously used for the provision of an enema, again with all of the above-noted advantages.

It is yet another object of the present invention to provide a method for manufacturing such an improved body fluid collecting bag.

The improved human body fluid collecting bag of the invention includes a main bag body formed of a synthetic plastic material and having an exterior, an interior, an operative end and an opposite sealed end, the operative end being provided with a resealable opening at an outer extent thereof. A foldable neck portion is received within the resealable opening in the operative end of the main bag body. The foldable neck portion has an inner extent and an oppositely arranged outer extent which define a closed interior space there between. The foldable neck portion is positionable between a retracted position within the bag interior and an extended position in which the outer extent of the neck portion extends outwardly from the resealable opening in exposed fashion. The resealable opening in the main bag body can be a ZIPLOCK® rib and channel type closure which is used to secure contents of the bag from spilling or leaking while being transported to a laboratory or while disposing of body waste fluids. The neck portion is provided with an inlet port for receiving an irrigating tube or probe, and an outlet port for sealing around the anus of a patient so that the irrigating tube can be fed through the neck portion of the bag body into the patient's rectum.

Preferably, the outlet port provided in the neck portion of the main bag body is provided with an adhesive seal. The inlet port is also preferably provided with an adhesive flap which can be used to seal the inlet port once the irrigating tube is withdrawn from the bag. The main bag body can conveniently be formed of a commercially available, synthetic polymeric material, such as polyvinyl chloride, having a transparent appearance so that any contents of the bag can be visualized. The main bag body can be provided with a carrying handle for transporting the bag and its contents. Preferably, the bag includes external marking indicia which functions as a measuring scale for providing a determination of the quantity of body fluid collected in the bag. The marking indicia can also include notations that identify the bag as containing body fluids and biohazard waste.

In the method of manufacturing a body fluid containing bag of the type described, the main bag body is formed by sealing opposing edges of the synthetic plastic material to form a main bag body having an exterior, an interior, an operative end and an opposite sealed end, the operative end being provided with a resealable opening at an outer extent thereof. The foldable neck portion of the bag is installed within the resealable opening in the operative end of the main bag body, the neck portion having an inner extent and an oppositely arranged outer extent which define a closed interior space therebetween. The inner extend can be fused within the bag interior or otherwise glued or joined to create a fluid seal. The foldable neck portion is initially positioned in a retracted position within the bag interior. The neck portion can be unfolded for use to an extended position in which the outer extent of the neck portion extends outwardly from the resealable opening in exposed fashion, as has previously been described. The neck portion is provided with an inlet port for receiving an irrigating tube and an outlet port for sealing around the anus of a patient so that the irrigating tube can be fed through the neck portion of the bag body into the patient's rectum.

Additional objects, features and advantages will be apparent in the written description which follows.

DETAILED DESCRIPTION OF THE INVENTION

Figure 1:
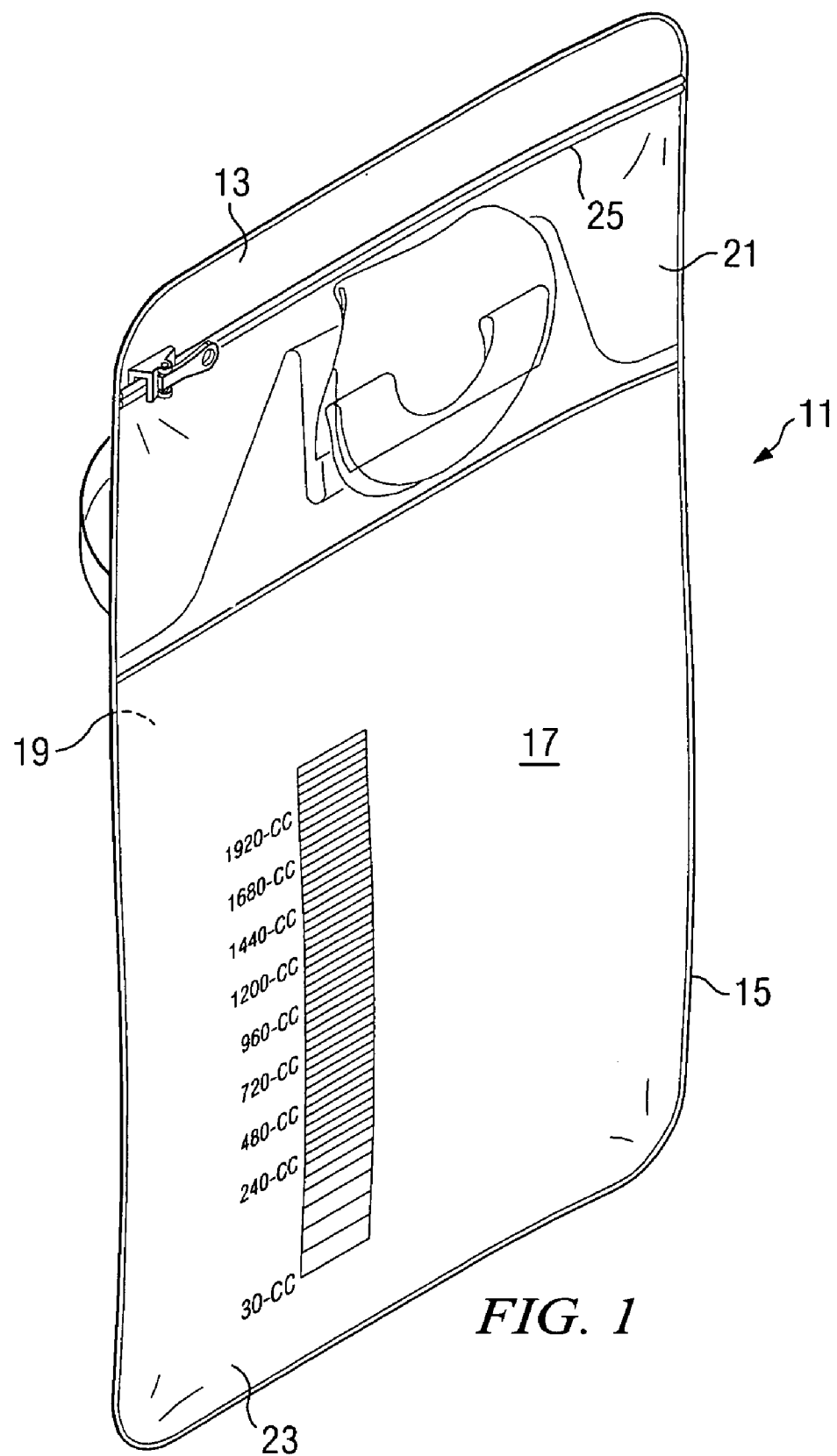
FIG. 1 is a planar perspective view of a human body fluid collecting bag of the invention showing one exposed planar surface thereof.

The improved body fluid collecting bag of the invention was developed to solve many of the difficulties and disadvantages inherent in the current types of human enema waste collecting bag technology. The improved collecting bag of the invention provides a new and improved way to collect human waste from patients, even in difficult situations. These situations include, but are not limited to, those patients that are unable to ambulate, sit upright or transfer to a bedside commode.

In this respect, before explaining the invention in detail, it is to be understood that the invention is not limited in its application to the details of construction or to the arrangements of the components set forth in the following description or illustrated in the drawings. The invention is capable of other applications and of being utilized in various ways. For example, the preferred embodiment of the invention is described as directed to an enema bodily fluid collecting device. However, the bag of the invention could also conceivably be used in collecting vomit, urine and other bodily fluids.

The various objects of the invention, along with the various features of novelty which characterize the invention, are pointed out with particularity in the claims annexed to and forming a part of this specification. For a better understanding of the invention, its operating advantages and the specific objects attained by its uses, reference should be had to the accompanying drawings and descriptive matter in which there is illustrated a particularly preferred embodiment of the invention.

Turning to FIG. 1, there is shown a human body fluid collecting bag of the invention, designated generally as 11. The bag 11 includes a main bag body 13 formed of a synthetic plastic or polymeric type material, such as a commercially available polyvinyl chloride. Preferably, the bag material is transparent so that any contents of the bag can be visualized and examined. The particular PVC material chosen for the bag illustrated in FIG. 1 is 12 mils thick and has peripheral edges 15 which are FDA heat seal approved (350° F.). The bag 11 also has an exterior 17, an interior 19, an operative end 21 and an opposite sealed end 23. The operative end 21 is provided with a resealable opening 25 adjacent an outer extent thereof. The preferred resealable opening is equipped with a PVC ZIPLOCK ® rib and channel type closure seal which is also FDA heat seal approved (350° F.). The seal is used to secure the contents of the bag from spilling or leaking while being transported to a laboratory or while disposing of body waste fluids.

Figure 2:
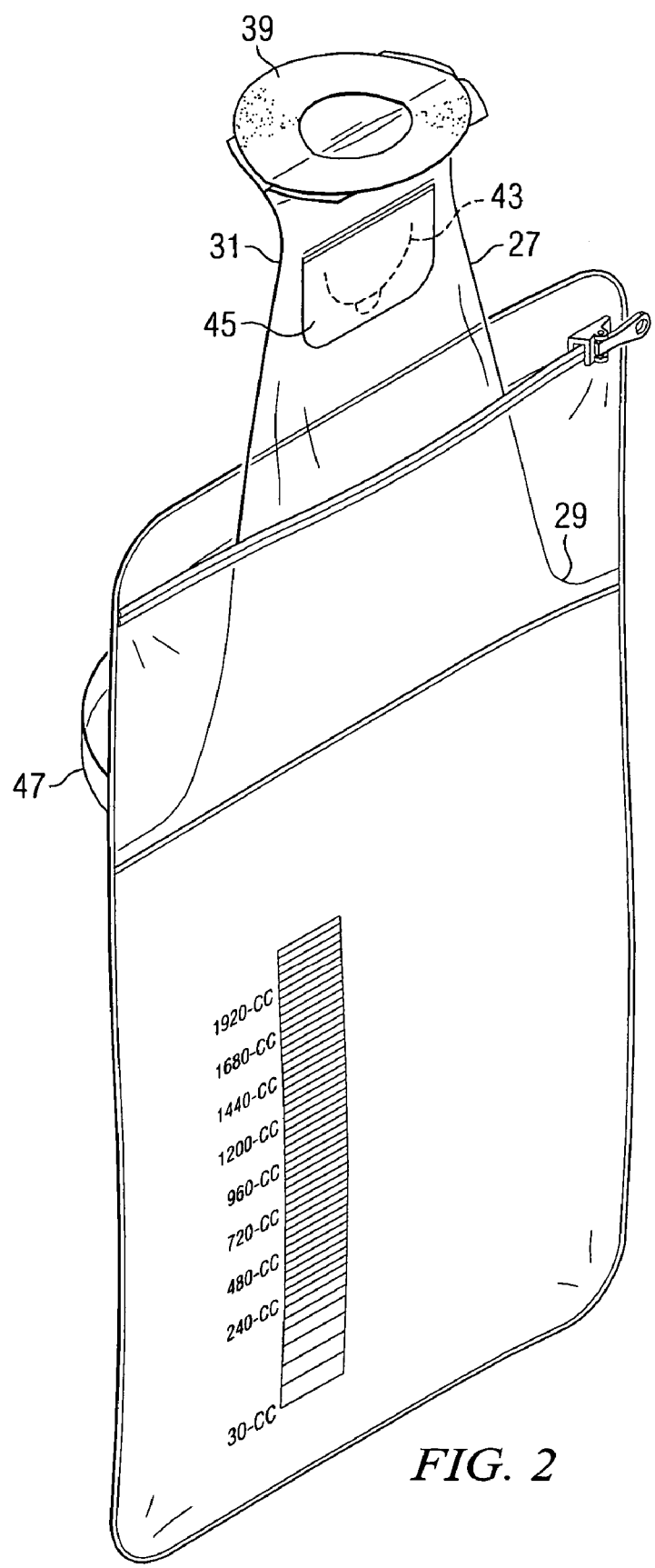
FIG. 2 is a view similar to FIG. 1, but showing the foldable neck portion of the bag in the extended position.

As illustrated in FIGS. 1 and 2, the bag body 13 is equipped with a foldable neck portion (shown exposed as 27 in FIG. 2). The neck portion 27 is positionable between a retracted position in which it is received within the resealable opening 25 in the bag interior (see FIG. 1), and an extended position in which the outer extent of the neck portion extends outwardly from the resealable opening in exposed fashion (see FIG. 2).

The neck portion 27 has an inner extent (29 in FIG. 2) which can be fused to the bag interior and an oppositely arranged outer extent 31 which define a closed interior space therebetween. When extended, as shown in FIG. 2, the interior space forms a funnel type cavity or space which communicates at the inner extent 29 with the remainder of the main bag body interior space.

Figure 3:
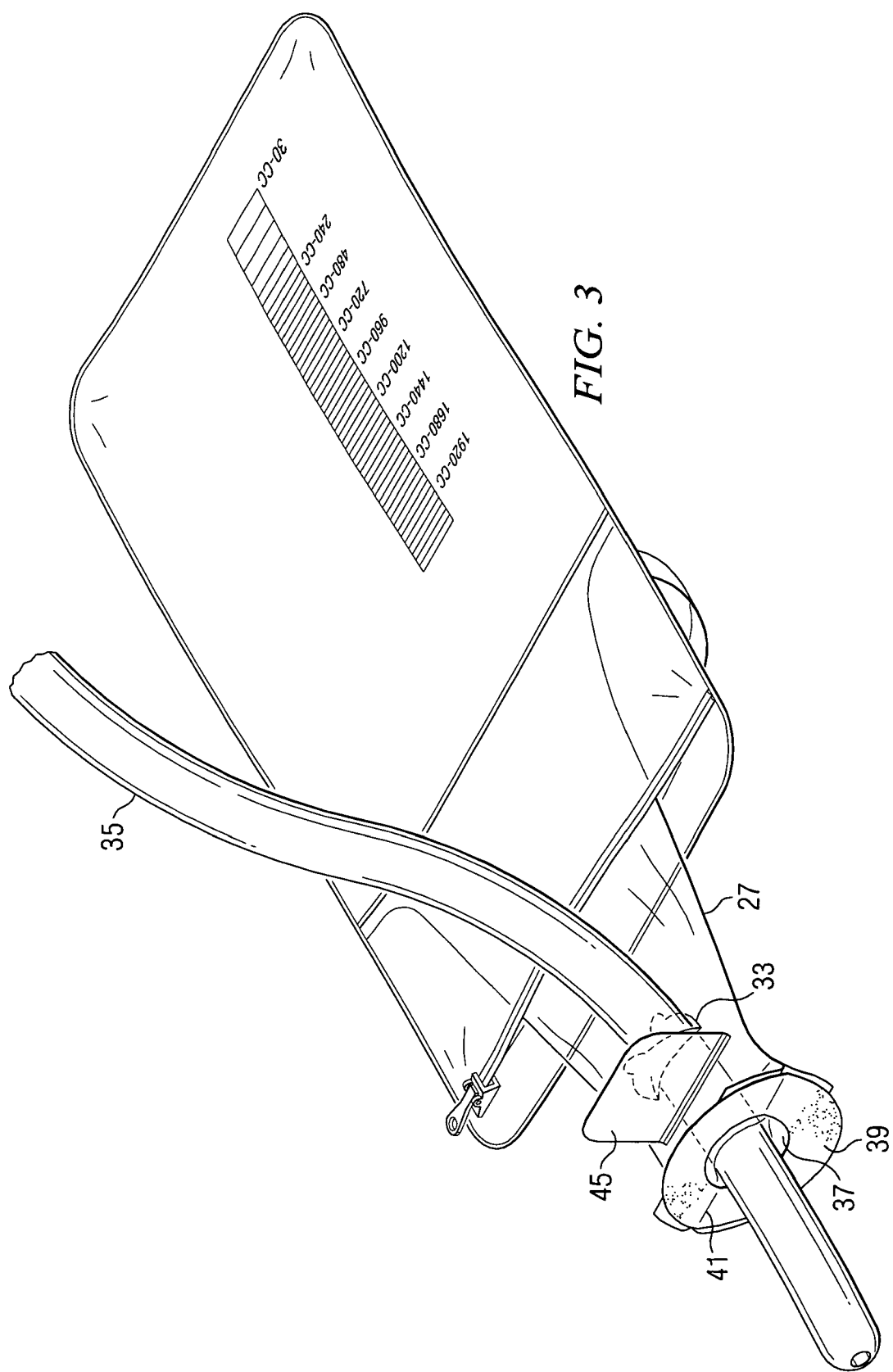
FIG. 3 is another view of the human body fluid collecting bag of FIG. 1, showing the insertion of the enema tube through the openings provided in the neck portion of the device.

As shown in FIGS. 2 and 3, the foldable neck portion 27 has an inlet port 33 for receiving an irrigating tube or probe (35 in FIG. 3) and an outlet port 37 for sealing around the anus of a patient so that the irrigating tube can be fed through the neck portion 27 of the bag body into the patient's rectum. The outlet port of the neck portion 27 is preferably provided with a seal means, such as the adhesive seal 39 shown in FIG. 3. The particular seal illustrated is a double sided adhesive seal pressure sensitive film coated 3 mil (#MED-6000). FIG. 2 shows the double sided adhesive covered with a protective, peel off material. FIG. 3 shows the temporary peel off material removed for use. As will be appreciated, the crease line 41 allows the adhesive seal to be resealed after use by simply folding the seal along the crease line.

The inlet port 33 of the foldable neck portion 27 is formed as a series of perforations (43 in FIG. 2). The series of perforation which forms the outline of the subsequently formed inlet port is also covered by a foldable flap 45. The flap 45, best seen in FIG. 3, is formed as an adhesive flap closure of pressure sensitive film coated 3 mil. In other words, the lower surface of the flap as viewed in FIG. 3 has a temporary protective peel of material in place as the bag is being used. Once the procedure is finished, the peel off label or backing is removed and the underlying adhesive region is used to seal against the perforated region of the inlet opening.

The bag can also be provide with certain external accessories and indicia. For example, the bag body 13 shown in FIG. 1 is provided with a carrying handle or strap 47 for conveniently transporting the bag and its contents. The handle can be formed of PVC and is FDA heat seal approved. The bag exterior can also be provided with Poly Ink compatible external marking indicia, for example, a graduated measuring scale (as at 49 in FIG. 1) which functions as a measuring scale for providing a determination of the quantity of body fluid collected in the bag. The external indicia can also comprise identifying indicia which identifies the bag as containing body fluids and thus biohazard waste, the ink being Poly Ink compatible.

Procedures to Administer An Enema Using the Bag of the Invention:

1. Properly position the patient.
2. Remove the foldable neck portion of the bag through the ZIPLOCK® rib and channel type closure and extend it outwardly to its fully extended position.
3. Open the perforated opening in the neck portion of the device to thereby form the inlet opening of the bag.
4. Remove the adhesive backing from the exterior surface of the seal region of the outlet port.

5. Apply the adhesive region of the outlet port to the rectum, forming a secure seal to the rectum.
6. Insert the enema tip through the perforated inlet opening out the outlet opening; and insert the tip into the rectum and instill the enema solution.
7. Remove the enema tip from the patient after the procedure has been completed at the perforated inlet opening and secure the adhesive flap closure over the inlet opening.

Procedures to Remove the Collection Bag:
1. Remove the rectum seal from the patient and fold the adhesive seal together along the crease line to thereby seal the outlet opening of the bag.
2. Roll the foldable neck portion of the bag into the bag interior through the ZIPLOCK ® rib and channel type closure and close the resealable opening.

An invention has been provided with a number of advantages. The use of the disposable collection bag of the invention will allow the caregiver to administer the enema and collect contents without contamination of the patient and/or the caregiver. The bag of the invention will collect all fecal materials and will provide a quantitative measurement of the bag contents for accurate records. The bag provides ease of clean-up following a therapeutic procedure, such as an enema, and disposal of the bag contents without risk of contamination to the patient or to the health care provider. The bag also prevents the body fluids/waste from contaminating bed linens and/or the patient. The bag identifies its contents as constituting a Biohazard Waste Bag and conveniently captures such wastes for disposal. The bag can be provided in a variety of different sizes, depending upon the ultimate application. Its use will also decrease cost of maintaining healthy skin by preventing secondary skin breakdown due to contact of fecal matter with patient's skin.

While the invention has been shown in only two of its forms, it is not thus limited but is susceptible to various changes and modifications without departing from the spirit thereof.

What is claimed is:

1. A method of using an enema body fluid containing bag in treating a human patient, the method comprising the steps of:
   forming a main bag body of a flexible synthetic plastic material, the main bag body having an exterior, an interior, an operative end and an opposite sealed end, the operative end being provided with a resealable opening at an outer extent thereof;
   providing a foldable neck portion which is received within the resealable opening in the operative end of the main bag body and having an inner extent and an oppositely arranged outer extent which define a closed interior space there between, the foldable neck portion being positionable between a retracted position within the bag interior and an extended position in which the outer extent of the neck portion extends outwardly from the resealable opening in exposed fashion;
   providing the neck portion with an inlet port for receiving an enema tube having an enema tip, the neck portion also having an outlet port for sealing around the anus of a patient so that the irrigating tube can be fed through the neck portion of the bag body into the patient's rectum;
   wherein the resealable opening which is provided in the main bag body is a rib and channel type closure which is used to secure contents of the bag from spilling or leaking while being transported to a laboratory or while disposing of body waste fluids;
   wherein the outlet port provided in the neck portion of the main bag body is provided with an adhesive seal having an adhesive backing;
   wherein the inlet port is also provided with an adhesive flap which can be used to seal the inlet port once the irrigating tube is withdrawn from the bag;
   removing the foldable neck portion of the bag through the rib and channel closure and extending it outwardly to an extended position;
   removing the adhesive backing from the adhesive seal on the outlet port and applying the adhesive region of the outlet port to the rectum of the patient, forming a secure seal to the rectum;
   inserting the enema tip through the inlet port in the neck portion of the bag and inserting the enema tip into the rectum of the patient, followed by instilling an enema solution; and
   removing the enema tip from the patient by withdrawing the enema tip through the inlet opening in the neck portion of the bag, followed by sealing the inlet opening with its adhesive flap.

2. The method of claim 1, further comprising the steps of:
   removing the rectum seal from the patient and folding the adhesive seal together along a crease line to thereby seal the outlet opening of the bag; and
   rolling the foldable neck portion of the bag into the bag interior through the channel and rib type closure and closing the resealable closure.

3. The method of claim 1, wherein the main bag body is formed of a synthetic polyolefin material having a transparent appearance so that any contents of the bag can be visualized,.

4. The method of claim 1, wherein the bag is provided with external marking indicia which functions as a measuring scale for providing a determination of the quantity of body fluid collected in the bag.

* * * * *